(12) United States Patent
Olson

(10) Patent No.: US 6,749,792 B2
(45) Date of Patent: Jun. 15, 2004

(54) MICRO-NEEDLES AND METHODS OF MANUFACTURE AND USE THEREOF

(75) Inventor: Lorin Olson, Scotts Valley, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 09/901,535

(22) Filed: Jul. 9, 2001

(65) Prior Publication Data

US 2003/0009113 A1 Jan. 9, 2003

(51) Int. Cl.$^7$ ................................................ B29C 45/00
(52) U.S. Cl. ..................... 264/328.1; 425/577; 164/464
(58) Field of Search ............................ 264/328.1, 144; 425/577; 164/464, 47

(56) References Cited

U.S. PATENT DOCUMENTS

| | | | |
|---|---|---|---|
| 3,964,482 A | | 6/1976 | Gerstel et al. |
| 4,838,877 A | * | 6/1989 | Massau ........................ 604/272 |
| 5,078,700 A | * | 1/1992 | Lambert et al. ............. 604/264 |
| 5,217,671 A | * | 6/1993 | Moriuchi et al. ........... 264/313 |
| 5,403,291 A | * | 4/1995 | Abrahamson ............... 604/523 |
| 5,456,875 A | * | 10/1995 | Lambert .................... 264/328.1 |
| 5,620,639 A | * | 4/1997 | Stevens et al. .............. 264/85 |
| 5,733,266 A | | 3/1998 | Gravlee, Jr. |
| 6,117,386 A | * | 9/2000 | Stiger .......................... 264/526 |
| 6,256,533 B1 | | 7/2001 | Yuzhakov et al. |
| 6,379,324 B1 | | 4/2002 | Gartstein et al. |
| 6,379,592 B1 | * | 4/2002 | Lundin et al. .............. 264/1.24 |
| 6,471,903 B2 | * | 10/2002 | Sherman et al. .......... 264/328.1 |
| 6,558,361 B1 | * | 5/2003 | Yeshurun .................... 604/272 |

FOREIGN PATENT DOCUMENTS

| | | |
|---|---|---|
| WO | WO 00/74763 | 12/2000 |
| WO | WO 01/49362 | 7/2001 |

OTHER PUBLICATIONS

Stoeber, Boris and Dorian Liepmann. "Two–Dimensional Arrays of Out–of–Plane Needles". Berkeley Sensor and Actuator Center, University of California at Berkeley. Given as a presentation Jun. 4–8, 2000.*

* cited by examiner

Primary Examiner—Michael Colaianni
Assistant Examiner—Monica A. Fontaine
(74) Attorney, Agent, or Firm—Carol M. LaSalle; Bozicevic, Field & Francis, LLP

(57) ABSTRACT

A micro-needle is provided which is particularly useful for the minimally invasive sampling of a biological fluid and/or the minimally invasive delivery of a drug or other formulation across the skin. The micro-needle has a structure having a base at a proximal end and a vertex at a distal end, and an open lumen extending there through and through which fluid may be transferred. The structure defines a structural axis that intersects the lumenal axis defined by the open lumen. The point of intersection between these axes is at a point below the vertex of the micro-needle to provide a sharp apex at the distal end of the micro-needle and defines the general configuration of the distal end of the micro-needle, which may be selected or customized depending on the intended use of the microneedle. The micro-needle may be integral with a measurement device for measuring the concentration of a constituent within sampled biological fluid and/or with a fluid reservoir for containing a fluid to be delivered, and may also be used in conjunction with a remote control means. Methods of making and using the micro-needle of the present invention as well as kits comprising one or more of the micro-needles are also provided.

18 Claims, 5 Drawing Sheets

MICRO-NEEDLES AND METHODS OF MANUFACTURE AND USE THEREOF

FIELD OF THE INVENTION

This invention is related to micro-needles, fabrication of micro-needles, and methods of using the micro-needles for obtaining biological fluid samples and for delivering drugs, agents, formulations or biological molecules across biological tissue barriers.

BACKGROUND

The detection of analytes in biological fluids is of ever increasing importance. Analyte detection assays find use in a variety of applications, including clinical laboratory testing, home testing, etc., where the results of such testing play a prominent role in the diagnosis and management of a variety of disease conditions. Common analytes of interest include glucose, cholesterol, and the like.

A common technique for collecting a sample of blood for analyte determination is to pierce the skin at least into the subcutaneous layer to access the underlining blood vessels in order to produce localized bleeding on the body surface. The accessed blood is then collected into a small tube for delivery and analyzed by testing equipment, often in the form of a hand-held instrument having a reagent sample onto which the blood sample is placed. The fingertip is the most frequently used site for this method of blood collection due to the large number of small blood vessels located therein. This method has the significant disadvantage of being painful because subcutaneous tissue of the fingertip has a large concentration of nerve endings. This technique of blood sampling also runs the risk of infection and the transmission of disease to the patient, particularly when done on a high-frequency basis. The problems with this technique are exacerbated by the fact that there is a limited amount of skin surface that can be used for the frequent sampling of blood. It is not uncommon for patients who require frequent monitoring of an analyte, to avoid having their blood sampled. With diabetics, for example, the failure to frequently measure their glucose level on a prescribed basis results in a lack of information necessary to properly control the level of glucose. Uncontrolled glucose levels can be very dangerous and even life-threatening.

Similarly, current methods of drug-delivery are invasive and suffer from the same disadvantages as current methods of biological fluid sampling.

To overcome the disadvantages of the above technique and others that are associated with a high degree of pain, certain analyte detection and drug delivery protocols and devices have been developed that use micro-needles, micro-piercing, or micro-cutting elements or analogous structures to penetrate the skin and other tissue barriers. Micro-needles may be combined with analyte measurement systems to provide a minimally invasive fluid retrieval and analyte sensing system. These systems may include one or more micro-needles that penetrate tissue to obtain body fluid samples.

Micro-needles are typically made from stainless steel or other metals. Metal needles are subject to numerous disadvantages. Some of the major disadvantages include the manufacturing complexities of metal needles, such as wire drawing, grinding, deburing and cleaning steps involved in the manufacturing process. Further, impurities in the metals can cause oxidation and deterioration of the needles. As such, the manufacturing process for metal micro-needles may also involve steps where impurities are eliminated from the metals. Another challenge is the difficulty in handling the micro-needles, which are very small and delicate, during each manufacturing step. It may be desirable to provide a certain feature, such as a customized or atypically designed needle tip, that is very difficult if not impossible to do in the conventional fabrication of metal needles. In such a case, the customized feature may require a means for providing or making such a feature which are not completely automated. Customization of metal micro-needles is difficult due to an increase in the number of steps involved in a manufacturing process, the cost of manufacturing and the probability for inconsistent products increase. As such, there is a need in the art for micro-needles that overcome the disadvantages of metal micro-needles.

Despite the work that has already been done in the area of micro-needles and the fabrication thereof, it is desirable to develop a micro-needle that is less expensive and easier to fabricate and customize.

SUMMARY OF THE INVENTION

Micro-needles and methods for making and using such micro-needles are provided for the sampling of biological fluid from tissue and/or for the delivery of drugs, etc. to within tissue. The subject micro-needles are useful in the context of analyte concentration measurement and is particularly suited for use in the measurement of glucose concentration in interstitial fluid. The subject micro-needles are also useful for the delivery of drugs for local or systemic therapy or diagnosis. Types of drugs and agents suitable for delivery with the devices of the present invention include, but are not limited to, nucleic acids, proteins, such as growth factors, and other agents such as antibiotics, steroids decongestants anesthetics, etc.

The subject micro-needle has a configuration optimized for minimally invasive sampling of biological fluids and, in particular, interstitial fluid sampling, as well as for the delivery of small doses of drugs or other formulations. A feature of the subject micro-needle is the superior sharpness of its distal tip which may be advantageous in minimizing and eliminating the pain felt by patients, for example, when delivering materials to or withdrawing materials from the skin.

The subject micro-needle is fabricated by means of micro-replication techniques, such as injection molding of a plastic material or the like. The plastic molded injection process allows flexibility in the design of the subject micro-needle and, in particular, allows it to be optimized or customized for a particular intended use.

The micro-needle of the present invention may be used in conjunction with a biological fluid sampling and analyte measuring device or system or with a drug or biological material reservoir or the like. The present invention further includes arrays of the subject micro-needle. Also provided by the present invention are methods of making, methods for using the micro-needle, and kits including one or more of the subject micro-needles or arrays thereof.

These and other features of the invention will become apparent to those persons skilled in the art upon reading the details of the present invention as more fully described below.

DETAILED DESCRIPTION OF PREFERRED EMBODIMENTS

Figure 1A:
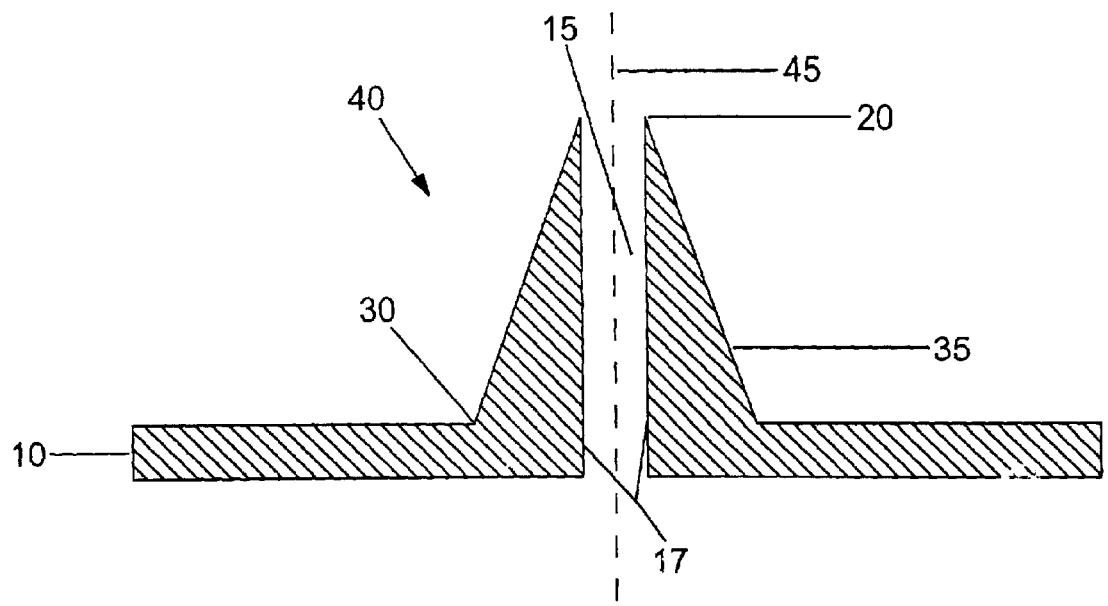
FIG. 1A is a cross-sectional view of a prior art micro-needle.

Before the present formulations and methods are described, it is to be understood that this invention is not limited to particular devices, formulas or steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a micro-needle" includes a plurality of such needles and reference to "the step" includes reference to one or more steps and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview of the Invention

In general, the subject micro-needle has a structure or a body having a customized configuration defined by a structure, such as an oblique cone (sometimes referred to as a "scalene cone") where the apex of the cone defines a distal end having a distal tip and the base of the cone defines the proximal or base end of the micro-needle structure. The distal tip has a sharp point for penetrating the skin surface and for accessing biological fluids therein. The micro-needle structure further includes a lumen which extends from the distal tip to the base end of the micro-needle and serves as a delivery conduit or channel for biological fluid accessed at the distal tip of the micro-needle. The diameter of the lumen is sized and configured to exert a capillary force on the biological fluid, thereby wicking it into the micro-needle structure. Alternatively, the fluid sampling or transport capabilities of the micro-needle may be accomplished by vacuum assist means.

The base end of the micro-needle may be placed in fluid communication with another structure, such as a means for measuring certain characteristics of sampled fluid or a reservoir for holding a drug or biological material for delivery across a biological barrier, e.g., skin. In the former embodiment, the micro-needle lumen acts to transfer wicked biological fluid into the measurement means, such as the reaction zone or chamber of an electrochemical cell, a porous structure containing a reagent material, or the like, commonly used in the detection and measurement of constituents within biological fluids. As such, the subject micro-needle may be integrally provided with such measurement means, collectively referred to as a "sensor device," for determining the concentration of a constituent within the sampled fluid. The subject sensor device may function as a part of an analyte sensing system that includes a means for controlling the sensor device.

In the fluid delivery embodiments of the present invention, the micro-needle lumen acts to transfer drugs, formulations or biological materials from a reservoir containing the fluid or material to be delivered. The subject micro-needle may be integrally provided with such a reservoir means, collectively referred to as a "delivery device." The subject delivery device may function as a part of a drug delivery system that includes a means for controlling, for example, the volume and rate of the material being delivered to the subject.

In certain other embodiments of the present invention, the micro-needles may be integrated in a single device having both sensor and delivery capabilities and means.

The subject micro-needles, sensor devices, delivery devices and systems are useful in the minimally invasive sampling of fluids, such as interstitial fluid, and the minimally invasive delivery of fluids, such as a drug or other agent. The sampling and sensor components and functions are particularly useful in the detection and measurement of various analytes, e.g., glucose, cholesterol, electrolytes, pharmaceuticals, or illicit drugs, and the like, present in the sampled fluid. The delivery components and functions are particularly useful in delivery an amount of drug, such as insulin, and the like, for treatment of a disease or condition, such as diabetes.

The Micro-needle

Figure 1B:
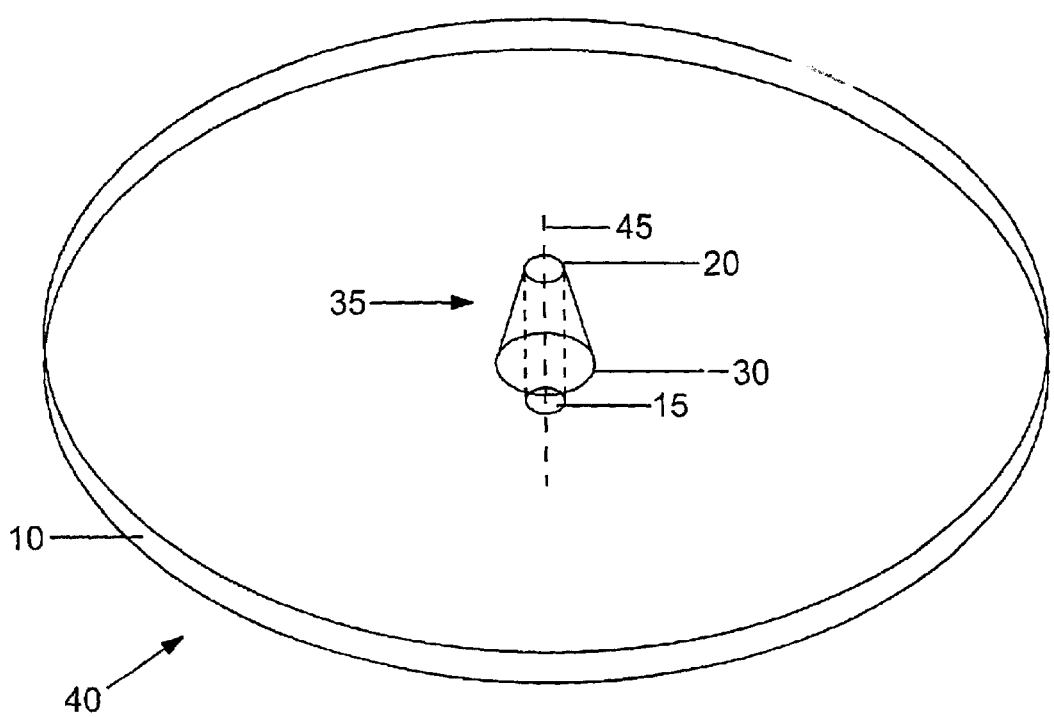
FIG. 1B is a top view of a prior art micro-needle.
Figure 2A:
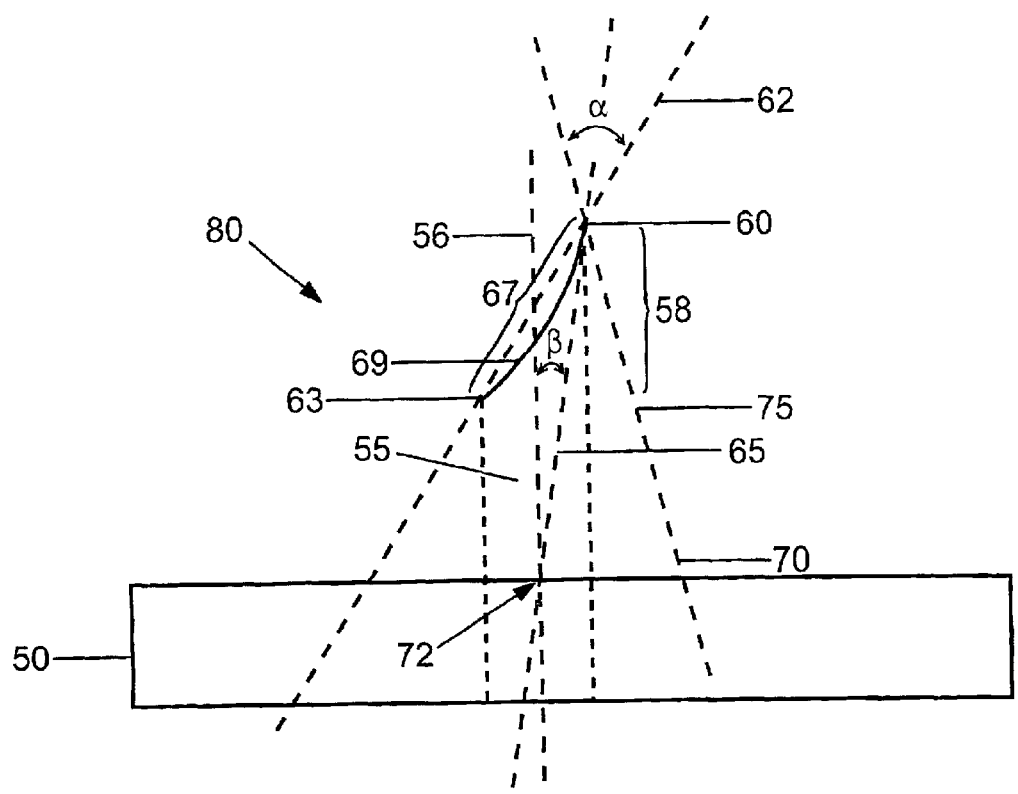
FIG. 2A is a cross-sectional view of a micro-needle according to the present invention.
Figure 2B:
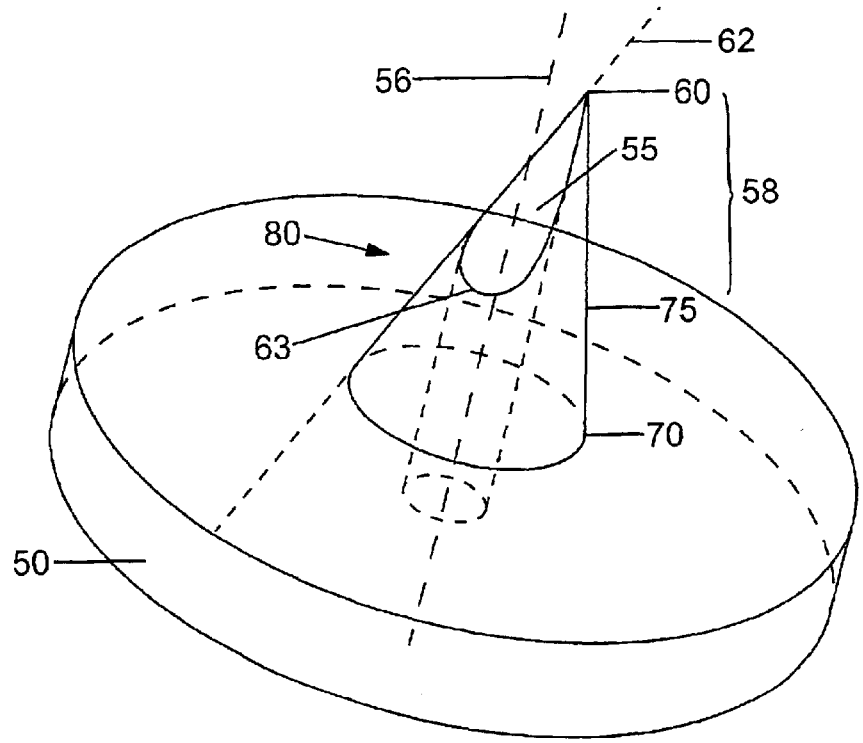
FIG. 2B is a top view of a micro-needle according to the present invention.

Referring now to the drawings, wherein like numerals indicate like elements, FIGS. 1A and 1B illustrate an exemplary prior art micro-needle 40 and FIGS. 2A and 2B illustrate one embodiment of a micro-needle 80 of the present invention.

FIGS. 1A and 1B illustrate cross-sectional and perspective views, respectively, of prior art micro-needle 40 having a frustum conical shape (i.e., a cone truncated by a plane parallel to its base) defining a longitudinal axis or centerline 45. Micro-needle 40 has a body 35 and a tip 20 at its distal end and a base 30 at its proximal end. The plane defined by the annular distal edge of tip 20 is generally substantially parallel to base 30.

Micro-needle 40 further includes a lumen 15 having the same longitudinal axis 45 as conically-shaped micro-needle body 35 (i.e., body 35 and lumen 15 are co-axial), extending from the distal end to the base 30 of micro-needle body 35. The walls 17 of lumen 15 are equidistant from centerline 45 along the entire length of lumen 15. In the illustrated embodiment, micro-needle 40 is operatively mounted and in fluid communication with a planar substrate 10, having sufficient rigidity to support micro-needle 40.

Micro-needle 40 generally has the following dimensions: a height ranging from about 50 to 3,000 $\mu$m, a luminal diameter ranging from about 10 to 200 $\mu$m and a base diameter ranging from about 100 to 400 $\mu$m.

The frustum conical shape of prior art micro-needle 40 is designed to penetrate the skin with a planar, annular footprint (i.e., the annular ring of the edge of the distal tip) which distributes the penetration force applied to micro-needle 40 over a surface area of the skin generally in the range from about 3,000 to 10,000 $\mu$m$^2$, depending on the desired depth of penetration. The greater the penetration surface area, the greater the force necessary to cause micro-needle 40 to disrupt the surface of the stratum corneum. The necessary penetration force increases as the number of micro-needles is increased. Thus, with an array of micro-needles 40, the amount of penetration force increases greatly. The greater the penetration force and the penetration surface area, the more pain likely to be felt by the patient. As such, it would be desirable to provide a micro-needle that has an extremely pointed and sharp tip with a footprint having a miniscule surface area, requiring very little force for the tip to disrupt the surface of the stratum corneum. As mentioned above, forming or creating such a tip is difficult with the micro-needle materials and fabrication processes of prior art.

Referring now to FIGS. 2A and 2B, there is shown cross-sectional and perspective views, respectively, of a micro-needle 80 according to the present invention. Micro-needle 80 includes a body 75 having a distal end 58 and a proximal end or base 70, and defining a structural or body axis 65 which extends from vertex 60 to the center 72 of base 70. Micro-needle 80 further includes an open lumen 55 that extends longitudinally from distal end 58 to base 70, defining a lumenal axis 56 of micro-needle 80 which is perpendicular to base 70.

The micro-needles of the present invention are characterized in part in that structural axis 65 and lumenal axis 56 are not co-axial. In many embodiments, body 75 has a substantially oblique shape defined by vertex 60 (also defined as the apex of micro-needle 80) at distal end 58, base 70, and the surface area defined between vertex 60 and base 70, defined, in part, by phantom line 62. An oblique structure is one that has a vertex or apex and a substantially flat base whose structural or body axis, i.e., the line extending between the vertex and the center of its base, is not perpendicular to the base. In other embodiments, body 75 may have a shape that is "regular" and not oblique, i.e., the line extending between the vertex and the center of its base is perpendicular to the base.

With either configuration, the resulting structure defines a vertex angle $\alpha$ and a structural or body axis 65, that extends from vertex 60 to the center 72 of base 70. Angle $\alpha$ is determined by the selected height and base diameter (or width) of micro-needle 80, discussed in more detail below, and may have any practical value for a selected application of the subject micro-needles. The volume of body 75 is determined by the height of vertex 60 and the diameter of base 70, discussed in further detail below. Here, base 70 has an annular-shaped cross-section (e.g., circular or elliptical), and as such, forming a conical-shaped oblique structure. Other configurations, such as pyramids wherein the base may have three or more sides (defining, e.g., a triangle, square, rectangular, etc.) or any appropriate non-annular cross-section, such as a polygonal shape, are also suitable for the micro-needles of the present invention.

Lumenal axis 56 intersects with structural or body axis 65 defining an intersection angle $\beta$ there between. For micro-needle embodiments having non-oblique configurations, the intersection angle $\beta$ is zero, i.e., lumenal axis 56 and structural axis 65 do not intersect but, instead, are parallel and not co-axial. For micro-needle embodiments having an oblique structure, the intersection angle $\beta$ is greater than zero (i.e., lumenal axis 56 and structural axis 65 are not co-axial nor are they parallel with each other) and has a value less than half of the vertex angle $\alpha$. In other words the vertex angle $\alpha$ is greater than twice the intersection angle $\beta$. This relationship is represented by the following equations:

$$\beta < \alpha/2 \text{ and } \alpha > 2\beta.$$

In addition to satisfying these equations, the micro-needle should have cone and wall strengths sufficient to withstand biological barrier penetration pressures for a given application.

Lumen 55 may have an annular or any suitable non-annular cross-sectional shape. As illustrated in FIG. 2B, lumen 55 has a cylindrical configuration. The wall defined by lumen 55 intersects with apex 60 to define the distal-most point of micro-needle 80. Diametrically opposite to apex 60, the lumenal wall intersects at a location 63 of micro-needle body 75 to define the most proximal point of distal end 58. The linear distance between apex 60 and proximal point 63 is indicated by bracket 67 of FIG. 2A. As such, an angled or sliced distal tip configuration is provided which facilitates easy penetration of apex 60 into the skin with minimal pressure applied to micro-needle 80, which may in turn reduce the pain felt by the patient. The angled distal tip may further be beveled or contoured along distance 67 between apex 60 and proximal point 63 to further facilitate penetration of micro-needle 80 into the skin.

In the illustrated embodiment of FIG. 2A, structural axis 65 of micro-needle 80 intersects lumenal axis 56 at a center 72 of base 70. However, other points of intersection between the two axes, i.e., the "axial intersection" (AI), either proximal to, i.e., below, or distal to, i.e., above, base 70, are within the scope of the present invention. This point of axial intersection determines, at least in part, the diameter of lumen 55, i.e., the distance 67 between apex 60 and proximal point 63. The intended use of the micro-needle and, more specifically, the desired fluid flow rate through lumen 55 (dependent upon the lumenal diameter) and the depth of penetration (dependent upon the lumenal length) dictates the relative location, i.e., proximal to base 70, at base 70, or distal to base 70, of the axial intersection of the subject micro-needles.

FIGS. 3A–D illustrate schematic representations of various embodiments of micro-needle lumen 55 and the portion of micro-needle body 75 defining apex 60 having different axial intersections; however, such are intended to be exemplary and are not intended to limit the possible locations of axial intersection. A feature of the micro-needles of the present invention is that such an axial intersection can occur at any point below apex 60. For simplicity only, the axial intersection for each embodiment will be discussed relative to the micro-needle base 70. In each embodiment, AI is the point of intersection between lumenal axis 56 and structural axis 65, wherein structural axis 65 is the line between apex 60 and the center point 95 of base 70.

Figure 3A:
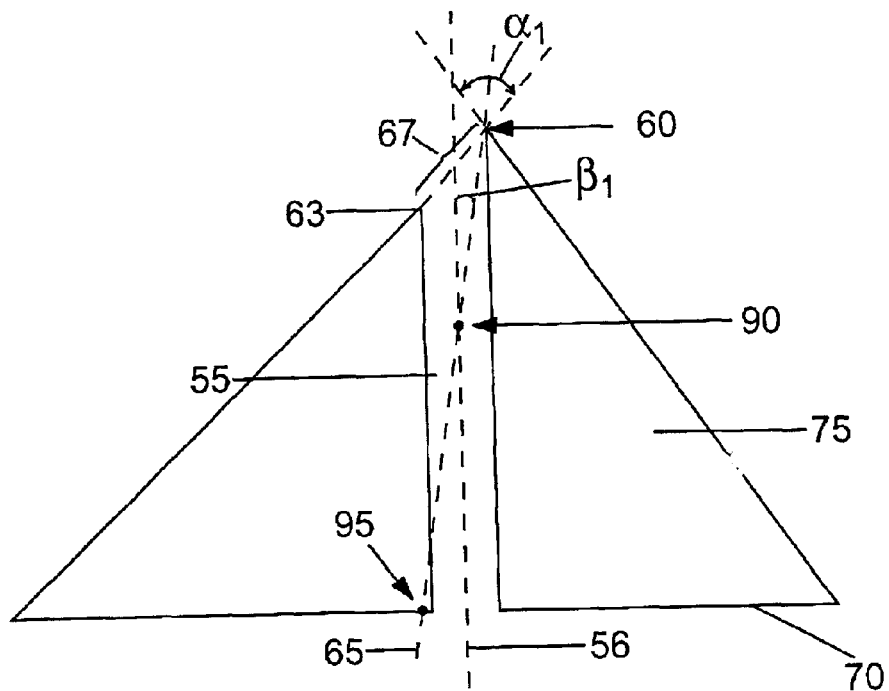
FIG. 3A is a two-dimensional schematic representation of one embodiment of a micro-needle according to the present invention wherein the structural axis and lumenal axis of the micro-needle intersect above the base of the micro-needle's oblique structure.
Figure 3B:
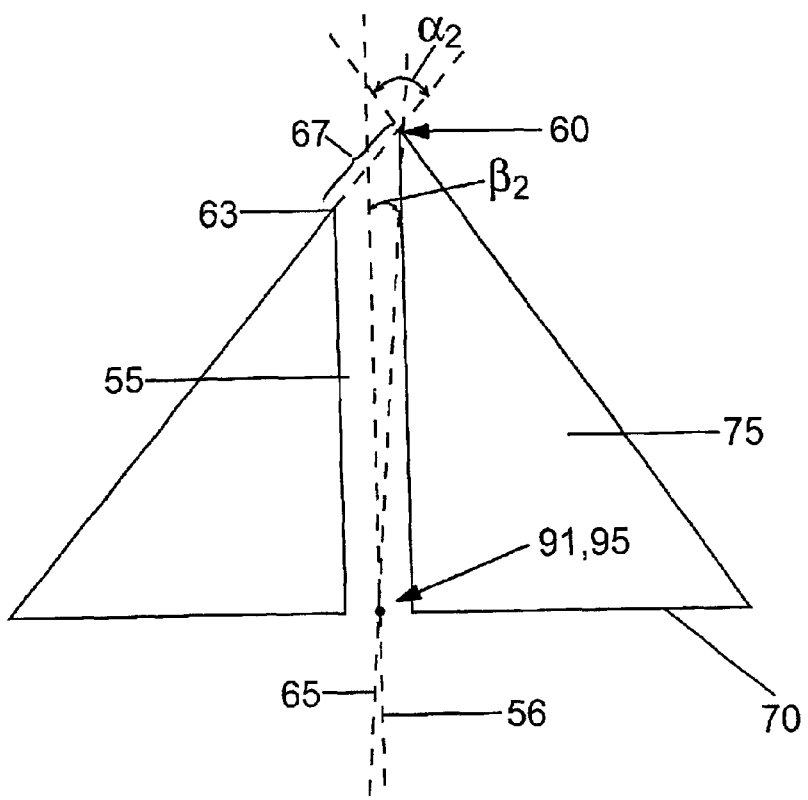
FIG. 3B is a two-dimensional schematic representation of another embodiment of a micro-needle according to the present invention wherein the structural axis and lumenal axis of the micro-needle intersect above the base of the micro-needle's oblique structure.
Figure 3C:
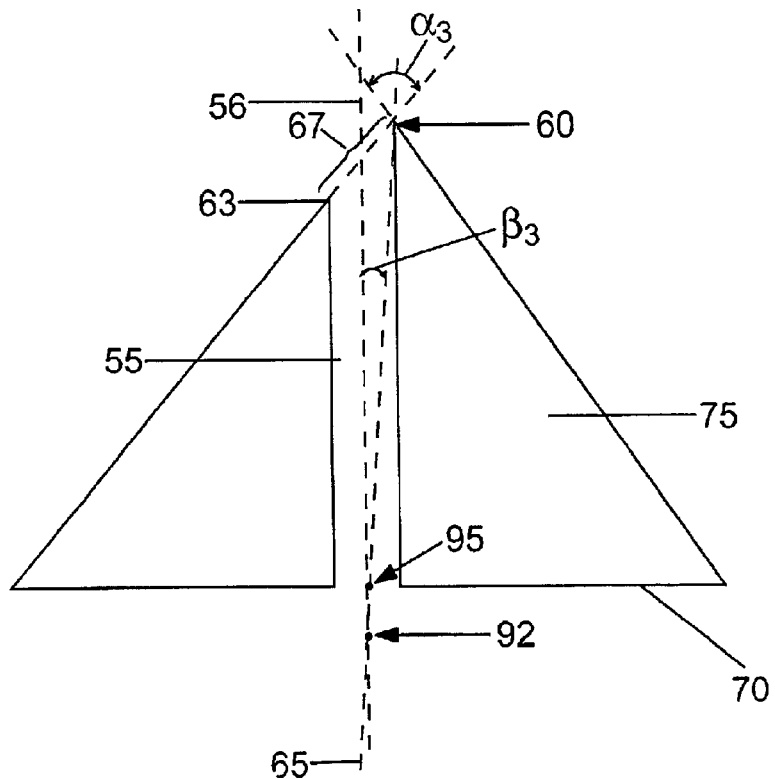
FIG. 3C is a two-dimensional schematic representation of another embodiment of a micro-needle according to the present invention wherein the structural axis and lumenal axis of the micro-needle intersect below the base of the micro-needle's oblique structure.

FIG. 3A illustrates an embodiment where AI 90 is above micro-needle base 70. Here, vertex angle α is defined as $\alpha_1$ and intersection angle β is defined as $\beta_1$. FIG. 3B illustrates an embodiment, such as the embodiment of FIGS. 2A and 2B, where AI 91 and the micro-needle base 70 are superimposed, i.e., lumenal axis 56 intersects structural axis 65 at a point along the plane which defines base 70. Here, vertex angle α is defined as $\alpha_2$ and intersection angle β is defined as $\beta_2$. FIG. 3C illustrates an embodiment where AI 92 is below micro-needle base 70. Here, vertex angle α is defined as $\alpha_3$ and intersection angle β is defined as $\beta_3$. Apparent from above-described FIGS. 3A–C, angles α and β both increase, respectively, as the AI approaches apex 60. As such, the distance 67 between apex 60 and proximal point 63 decreases. Conversely, as the AI moves away from apex 60, angles α and β both decrease, respectively, and distance 67 increases.

Figure 3D:
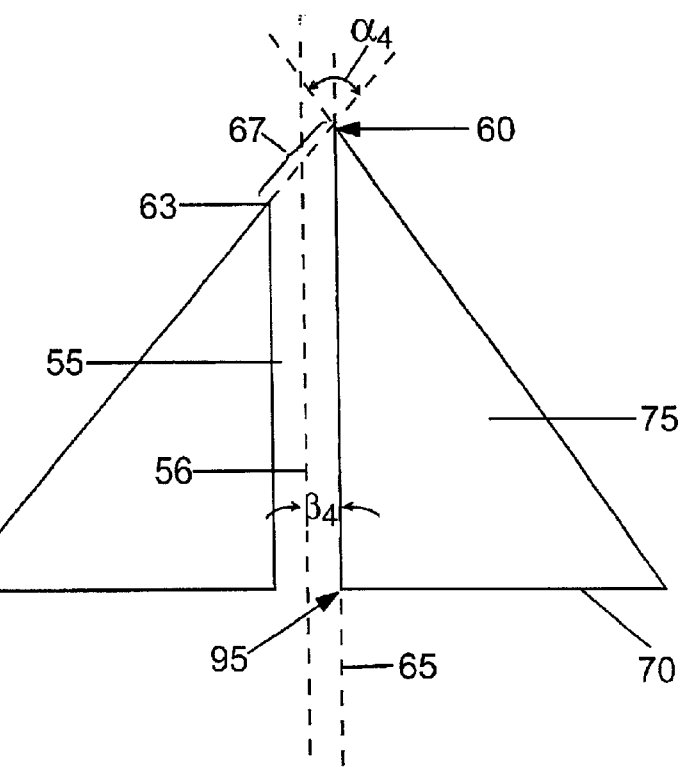
FIG. 3D is a two-dimensional schematic representation of another embodiment of a micro-needle according to the present invention wherein the structural axis and lumenal axis of the micro-needle are parallel to each other.

FIG. 3D illustrates an embodiment where angle $\beta_4=0$ and angle $\alpha_4$ has any suitable value for minimally invasive penetration through a biological barrier. As such, angle α preferably ranges from about 30 to 60° but may be more or less depending on the particular application.

The micro-needles of the present invention may have the following dimensions: a height or length generally in the range from about 100 to 10,000 μm, usually in the range from about 200 to 2,000 μm, and more usually in the range from 500 to 1,200 μm although the actual penetration depth of the micro-needle may be less; a base diameter generally in the range from about 100 to about 2,000 μm, and typically in the range from about 100 to 600 μm, and more typically in the range from about 250 to 500 μm; and a lumenal diameter capable of exerting a capillary force on fluid and, thus, is generally in the range from about 10 to 200 μm and more typically in the range from about 70 to 150 μm. Any appropriate aspect ratio between the height and base diameter of the micro-needle may be used, however, the aspect ratio is at least 1:1, and is usually between about 2:1 to 5:1.

Materials

The subject micro-needles are configured to be mechanically stable and strong enough to penetrate the stratum corneum. Preferably, the micro-needles are made of a biocompatible material so as not to cause irritation to the skin or an undesirable tissue response. In certain embodiments, the micro-needles are made of a plastic or resin material. Specific examples of such materials include, but are not limited to, acrylic, polyacrylates, polycarbonate, epoxies, polyesters polyetheretherketone, polyvinylchloride, polyolefins, liquid crystalline polyesters, or their composites. In other embodiments, the subject micro-needles may be made of any suitable solid material, including stainless steel and other metals, provided such material is suitable for treatment in a micro-replication process.

Micro-needle(s) Integrated with Sensor and/or Delivery Devices

The micro-needles of the present invention may be integrally provided with a measurement means to provide a fluid sampling and constituent measurement device, also referred to as a "sensor device", for determining the concentration of one or more constituents within a sampled fluid. Alternatively, the subject micro-needles may be integrally provided with a reservoir chamber for holding drugs or the like for the delivery of such for therapeutic and/or diagnostic applications. Additionally, the micro-needles may be integrated with a device which includes both fluid sampling/measurement means and fluid holding/delivery means.

FIGS. 2A and 2B schematically illustrate such an integral device. Micro-needle 80 is operatively mounted or affixed to a substrate 50 or the like which may house, for example, an analyte measurement means (not shown) and/or a fluid reservoir (not shown). The measurement means may include an electrochemical means, a photometric means or any other suitable means for measuring the level of a target constituent (s). The fluid reservoir may include a chamber containing a selected volume or one or more doses of a drug or other material.

Lumen 55 of micro-needle 80 is shown in fluid communication with pore 52 of substrate 50 having the same or substantially the same diameter dimensions as lumen 55. As such, substrate housing an analyte measurement means is able to receive a sampled biological fluid through lumen 55 by means of a capillary force when micro-needle 80 is penetrated within the skin. With delivery devices of the present invention, pore 52 and lumen 55 may have the same or different diameter dimensions, depending on the desired delivery protocol.

In certain embodiments, the sensor/delivery device may provide at least one subject micro-needle 80, or multiple micro-needles in the form of an array in which the micro-needles are mounted to or formed on, in close proximity with each other, to a base structure or substrate. The micro-needles and the associated substrate may be separately fabricated components which are integrally connected or may be formed together to establish a single, generally continuous device if desired.

Any suitable number of micro-needles may be employed with the sensor/delivery devices of the present invention. The optimal number will depend upon various factors including the type of fluid being sampled or delivered, the location and surface area of the biological tissue into which the micro-needles are inserted, the rate of sampling or delivery desired, the size of the device and the margin of accuracy desired. Regardless of the number micro-needles, they are sufficiently separated from each other so as to ensure that the stratum corneum can be penetrated without undue pressure on the skin. In general, micro-needles are separated from adjacent micro-needles a distance in the range from about 100 to about 1,000 μm, and typically from about 200 to 600 μm. Additionally, the micro-needle array may comprise micro-needles of the present invention having varying shapes, lengths, widths and tip configurations.

The subject sensor/delivery devices may be part of a system for sampling biological fluid and measuring the target analyte concentration therein or for deiverying therapeutic or diagnostic materials across a biological tissue barrier. Such a system of the present invention may include a control unit for automatically controlling the function of the sensor/delivery device and for deriving specific information about the sampled fluid and its constituents and for displaying such information and/or for controlling the volume and rate of delivery of a fluid. For example, the control unit may be configured to generate and send input signals to the sensor/delivery device and to receive output signals from the sensor/delivery device. These functions, among others, may be controlled by a software algorithm programmed within the control unit. With such a control unit, functions such as the automatic calculation of the concentration of a target analyte in a biological sample such that a user need only insert a micro-needle of the subject invention into the skin and then read the final analyte concentration result from a display of the device. Such a control device is further described in U.S. Pat. No. 6,193,873 entitled "Sample Detection to Initiate Timing of an Electrochemical Assay," the disclosure of which is herein incorporated by reference.

Methods of Manufacture

As mentioned above, the micro-needles of the present invention are fabricated by micro-replication technology using any solid material. As mentioned previously, suitable materials include, but are not limited to, plastics, polymers or resins, and the like which are suitable for forming components by means of injection molding. Other solid materials, suitable for use in micro-replication technology, may also be used to form the micro-needles and devices of the present invention.

Plastic injection molding is one type of micro-fabrication technique which is particularly suitable for fabricating the micro-needles of the present invention. An advantage of plastic injection molding is the ability to customize and precisely detail a micro-needle for its intended application far more quickly than by prior art micro-needle fabrication techniques. In particular, the oblique structures, beveled tips and sharp points or apexes of the subject micro-needles discussed above may be fabricated by plastic injection-molding techniques in an automated fashion.

In plastic injection molding, plastic resins and polymers are typical materials used in the form of pellets or small particles. Particularly suitable resins and polymers include, but are not limited to, polyacrylate, polycarbonate, epoxies, polyester, polyetherether-ketone, polyvinylchloride, polyolefins, liquid crystalline polymers, polyphenylene sulfide, polyphenylene oxide, polyacetal, polyimide, polyamide, polystyrene, copolymers or their composites or the like. These pellets or particles are fed into an injection molding machine and heated until they become molten. The molten material is then forced into a mold having a reverse image of the micro-needle structure to be formed. The molten material is then allowed to cool and become solidified within the mold. The resulting solid structure is then ejected from the mold by means of ejection pins which are run through the mold.

Figure 4A:
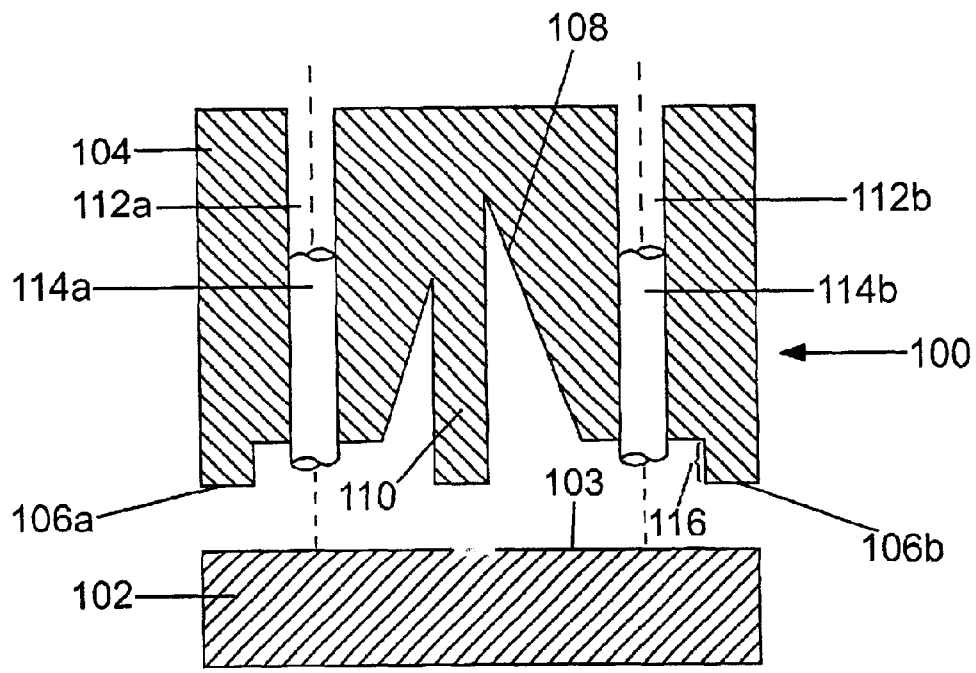
FIG. 4A is a cross-sectional view of one embodiment of a mold suitable for use in the fabrication of the micro-needles of the present invention.
Figure 4B:
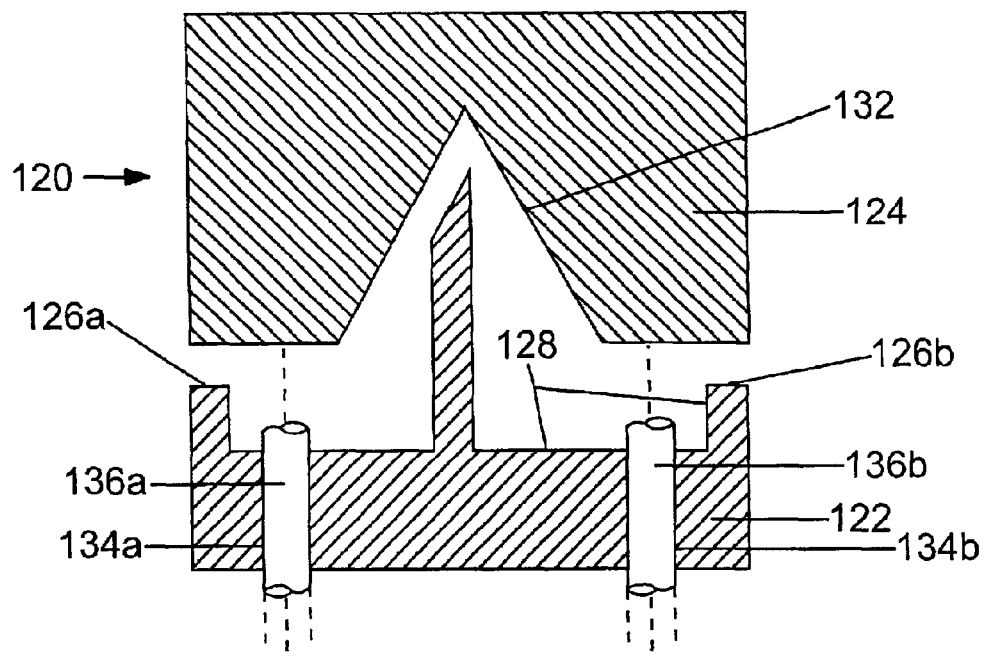
FIG. 4B is a cross-sectional view of another embodiment of a mold suitable for use in the fabrication of the micro-needles of the present invention.

Another micro-replication technique suitable for fabricating the micro-needles of the present invention is powder injection molding. In this fabrication process, a mold is provided having a cavity resembling the negative image of the micro-needle device. FIGS. 4A and 4B illustrate cross-sections of exemplary embodiments of molds that are suitable for use in the injection molding of the micro-needles of the present invention.

FIG. 4A shows a mold assembly 100 having a base portion 102 and structural portion 104 which are alignable in a sealing engagement with each other at rests 106a and 106b. Base portion 102 provides a surface area 103 which forms either the base end of a micro-needle or, as here, the back-side of a substrate structure, such as those described above. Structural portion 104 provides a negative image of the desired micro-needle structure 108, such as the micro-needles structures of the present invention. Structural portion 104 also provides a pin formation 110 within micro-needle structure 108 which forms the lumen within the micro-needle structure as well as provides a spacing 116 forming the structure and side walls of a substrate. Through structural portion 104 and parallel with its y-axis are bores 112a, 112b for receiving and guiding ejection pins 114a, 114b, respectively. Pins 114a, 114b serve to eject the molded structure off of structural portion 104.

FIG. 4B illustrates another embodiment of a mold 120 having base portion 122 and structural portion 124 which are alignable in sealing engagement with each other at rests 126a and 126b. Structural portion 124 provides a negative or opposite image of the desired micro-needle structure 132, such as the micro-needles structures of the present invention. Base portion 102 provides a surface area 128 which forms either the base end of a micro-needle or, as here, the back-side and side walls of a substrate structure, such as those described above. Additionally, base portion 122 also provides a pin formation 130 for forming a lumen within micro-needle structure 132. Through base portion 122 and parallel with its y-axis are bores 134a, 134b for receiving and guiding ejection pins 136a, 136b, respectively. Pins 136a, 136b serve to eject the molded structure off of base portion 122.

Next, a granulated material is selected for filling the mold cavities. Suitable materials for powder injection molding are metals, silicon carbide, silicon oxide, aluminum oxide, zirconium oxide, and their mixtures. The granulated particles are then mixed with a binder material and heated to a high temperature until molten, then transferred into a mold, such as the molds of the present invention described above. The molten material is then allowed to cool and harden. The hardened structure is then removed from the mold, such as by means of the ejection pins discussed above, and placed in a solvent ore material to extract the binder material from the resulting structure. The structure is then further hardened by means of a sintering process.

The cavities of the molds used in the above-described fabrication processes may be formed in the desired negative or opposite image, e.g., an oblique cone shape, of a micro-needle by means of an electrical discharge machining (EDM). In this process, an electrode is used to cut or form the desired configuration of a micro-needle structure into the base and structural portions of the mold. The formation pin used to form the micro-needle lumen may be formed by the EDM process or, alternatively, formed by a modular pin fastened within the cavity of either the base or structural portions of the mold.

The present invention also provides for a method of manufacturing tiny oblique structures. These oblique structures have a base end and a vertex end. The base end has a diameter generally in the range from about 100 to 2,000 $\mu$m and more typically in the range from about 100 to 500 $\mu$m. The base-to-vertex height is generally in the range from about 100 to 10,000 $\mu$m, and more typically in the range from about 200 to 2,000 $\mu$m.

This method includes providing a suitable material from which said oblique structure can be fabricated by means of one or more micro-replication techniques, such as the injection molding technique and electrical discharge machining discussed above. The manufacturing process further includes forming an open lumen within the oblique structure either in conjunction with the fabrication of the oblique structure or thereafter. The open lumen is formed to extend from the base end of the structure to the vertex end and may have dimensions the same as or similar to those discussed with respect to the micro-needle embodiment of FIGS. 2A and 2B. The process additionally includes customizing a tip at the vertex end of the structure. Again, such customization may be performed in conjunction with the fabrication of the oblique structure and/or in conjunction with the fabrication of the open lumen within the oblique structure. The customized tip may be selectively beveled, for a particular application, such as those mentioned above.

Methods of Using

Methods for using the subject micro-needles in the context of biological fluid sampling and/or the delivery of a material across a biological tissue barrier are also provided by the present invention. In practicing these methods, the first step is to provide a device having one or more subject micro-needles or an array of subject micro-needles, as described above. The subject micro-needle(s) may be made of material formed by a micro-replication technique, such as plastic injection molding. More specifically, that material may be a type of plastic, polymer or resin.

In the context of biological fluid sampling and testing applications, the micro-needle(s) may be provide as an integral part of a subject sensor device, which device may be particularly configured (i.e., containing the appropriate reagent) for targeting the analyte(s) of interest. In certain embodiments, the sensor device may be a stand alone device, while in other embodiments of the present invention, the sensor device may be operatively engaged and interfaced with a control unit, described above, that can be manually held and controlled by the user. The control unit is programmed for testing the targeted analyte(s). In either case, the user positions sensor device over a selected area of the patient's skin and, with slight pressure, the micro-needle(s) of the sensor device is/are caused to penetrate into the skin. The depth to which the micro-needles are inserted will depend on the length of the respective micro-needles or by some other means associated with the sensor unit for limiting the insertion depth.

Upon insertion into the patient's skin, an amount (i.e., a sample) of biological fluid present at the open tips of the micro-needles is wicked into the lumen by means of a capillary force, or by a vacuum assist device or the like. The sampled fluid is then transported to a measurement area, e.g., a reaction zone of an electrochemical cell, of the measurement means. A signal producing and receiving system of the measurement means, defined by the type of measurement being made, e.g. electrochemical or photometric, measures the concentration of the analyte within the sampled fluid. Different analytes of interest may be detected using the subject systems. Representative analytes include glucose, cholesterol, lactate, alcohol, and the like.

In the context of drug or biological material delivery applications, the micro-needle(s) may be provide as an integral part of a delivery device containing a reservoir for holding a volume of drug or material to be delivered, which device may be particularly configured for controlling the rate of delivery such drug or material. In certain embodiments, the delivery device may be a stand alone device, while in other embodiments of the present invention, the delivery device may be operatively engaged and interfaced with a control unit, described above, that can be manually held and controlled by the user. The control unit may be programmed for delivering a selected amount of drug or material to be delivered. In either case, the user positions the delivery device over a selected area of the patient's skin and, with slight pressure, the micro-needle(s) of the delivery device is/are caused to penetrate into the skin. The depth to which the micro-needles are inserted will depend on the length of the respective micro-needles or by some other means associated with the delivery device for limiting the insertion depth.

Upon insertion into the patient's skin, an amount of the drug or material held within the delivery devices reservoir is injected or is otherwise caused to be transported via the micro-needle(s) to within the biological tissue. Various drugs and materials to be delivered include therapeutic drugs diagnostic agents, genetic material biological material, and the like.

Kits

Also provided by the subject invention are kits for use in practicing the subject methods. The kits of the subject invention include at least one subject micro-needle and/or one or more subject sensor and/or delivery devices having one or more subject micro-needles. The sensor/delivery devices may include an array of micro-needles of the present invention having the same or different lengths. Certain kits may include various sensor devices each containing the same or different reagents. Also, more than one reagent may be provides within a single micro-needle array, wherein one or more of the micro-needles are provided with a first reagent for testing a first target analyte and one or more other micro-needles are provided with other reagents for testing other targeted analytes. Other kits may include various delivery devices each containing the same or different drug or formulation. The kits may also include a reusable or disposable control unit that may be used with reusable or disposable sensor/delivery devices of the kit of the subject invention. Finally, the kits preferably include instructions for using the subject devices in the determination of an analyte concentration in a biological sample and/or for delivering a drug or formulation across a biological barrier. These instructions may be present on one or more of the packaging, a label insert, or containers present in the kits, and the like.

It is evident from the above description that the features of the subject micro-needles overcome many of the disadvantages of prior art micro-needles, and provide certain advantages including, but not limited to, providing micro-needles having extremely sharp tips for penetration into the skin, providing a customized micro-needle for the particular application at hand and providing easier and less costly manufacturing techniques. Other advantages of the subject micro-needles is the reduction in pain experienced by a patient as a result of the reduced footprint of the micro-needle tip and the minimal pressure required to cause the micro-needle to penetrate the skin. As such, the subject invention represents a significant contribution to the field of fluid sampling and delivery across a biological barrier.

The subject invention is shown and described herein in what is considered to be the most practical, and preferred embodiments. It is recognized, however, that departures may be made there from, which are within the scope of the invention, and that obvious modifications will occur to one skilled in the art upon reading this disclosure.

The specific devices and methods disclosed and the applications, biological fluids and constituents, drugs and formulations discussed herein are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. A method of manufacturing a micro-needle structure for penetrating the skin and other tissue barriers, said method comprising:

providing a suitable material from which said micro-needle structure can be fabricated by at least one micro-replication technique;

fabricating said micro-needle structure from said suitable material by said at least one micro-replication technique, wherein said micro-needle structure comprises a conical configuration comprising a proximal end defining a base having a center and a distal end having a vertex comprising a sharp tip, wherein said base has a diameter in the range from about 100 to 2,000 $\mu$m and wherein a line extending from said center of the base to said vertex defines a structural axis having a length in the range from about 100 to 10,000 $\mu$m and forming open lumen within said micro-needle structure, said open lumen defining a lumenal axis and extending from said base to said vertex, wherein a distal end of said open lumen intersects said vertex and wherein said lumenal axis and said structural axis intersect at an intersection angle.

2. The method of claim 1, wherein said open lumen is formed during the step of fabricating.

3. The method of claim 1 further comprising forming a selectively angled tip at said vertex.

4. The method of claim 1 wherein said suitable material is chosen from the group of a plastic and a resin.

5. The method of claim 1 wherein said suitable material is chosen from the group of acrylic, polyacrylates, polycarbonate, epoxies, polyesters polyetheretherketone, polyvinylchloride, polyolefins and liquid crystalline polyesters.

6. The method of claim 4 wherein said at least one micro-replication technique comprises injection molding.

7. The method of claim 1 wherein said suitable material comprises a metal.

8. The method of claim 1 the diameter of said open lumen is configured to exert a capillary force on a fluid present at said distal end of said open lumen.

9. The method of claim 1, wherein said vertex defines a vertex angle wherein said vertex angle is greater than twice the intersection angle.

10. The method of claim 3 wherein said selectively angled tip comprises a beveled edge.

11. A method of manufacturing a micro-needle structure, said method comprising:

providing a plastic material;

fabricating said micro-needle structure by injection molding said plastic material, wherein said micro-needle structure comprises an oblique cone configuration having a base and a vertex comprising a sharp tip;

forming an open lumen within said micro-needle structure, said open lumen extending from said base to said vertex wherein a distal end of said open lumen intersects said vertex; and wherein said vertex defines a vertex angle, a line extending from a center of said base to said vertex defines a structural axis, and said open lumen defines a lumenal axis, wherein said lumenal axis and said structural axis intersect at an intersection angle.

12. The method of claim 11, wherein:

said vertex angle is greater than twice the intersection angle.

13. A method of manufacturing a device comprising a micro-needle structure, said method comprising:

providing a suitable material from which said micro-needle structure can be fabricated by at least one micro-replication technique;

fabricating said micro-needle structure from said suitable material by said at least one micro-replication technique, wherein said micro-needle structure comprises an oblique cone configuration having a base and a vertex configured for penetrating the skin and other tissue barriers;

forming an open lumen within said micro-needle structure, said open lumen extending from said base to said vertex wherein a distal end of said open lumen intersects said vertex;

wherein said vertex defines a vertex angle, a line extending from a center of said base to said vertex defines a structural axis, and said open lumen defines a lumenal axis, wherein said lumenal axis and said structural axis intersect at an intersection angle, and integrating said micro-needle structure with another structure wherein said open lumen is in fluid communication with said other structure.

14. The method of claim 13, wherein said other structure comprises provided with means for receiving fluid and measuring a constituent of fluid received therein.

15. The method of claim 13, wherein said other structure comprises a chamber for holding a fluid therein.

16. The method of claim 15, wherein said fluid is a therapeutic agent.

17. The method of claim 13, further comprising fabricating a plurality of said micro-needle structures and integrating said plurality with said other structure wherein said open lumen of each said micro-needle structure is in fluid communication with said other structure.

18. The method of claim 13, wherein:

said vertex angle is greater than twice the intersection angle.

* * * * *